(12) United States Patent
Wu et al.

(10) Patent No.: US 11,664,208 B2
(45) Date of Patent: May 30, 2023

(54) METHOD FOR SIMULTANEOUSLY MEASURING THE VALUE OF FORSTERITE AND TRACE ELEMENTS IN OLIVINE

(71) Applicant: INSTITUTE OF GEOLOGY AND GEOPHYSICS, CHINESE ACADEMY OF SCIENCES, Beijing (CN)

(72) Inventors: Shitou Wu, Beijing (CN); Yadong Wu, Beijing (CN); Yueheng Yang, Beijing (CN); Hao Wang, Beijing (CN); Chao Huang, Beijing (CN); Liewen Xie, Beijing (CN)

(73) Assignee: INSTITUTE OF GEOLOGY AND GEOPHYSICS, CHINESE ACADEMY OF SCIENCES, Beijing (CN)

( * ) Notice: Subject to any disclaimer, the term of this patent is extended or adjusted under 35 U.S.C. 154(b) by 266 days.

(21) Appl. No.: 17/097,961

(22) Filed: Nov. 13, 2020

(65) Prior Publication Data
US 2021/0358731 A1 Nov. 18, 2021

(30) Foreign Application Priority Data
May 13, 2020 (CN) .......................... 202010404435.8

(51) Int. Cl.
| | |
|---|---|
| H01J 49/00 | (2006.01) |
| G01N 33/24 | (2006.01) |
| H01J 49/04 | (2006.01) |
| H01J 49/10 | (2006.01) |
| H01J 49/16 | (2006.01) |

(52) U.S. Cl.
CPC .......... *H01J 49/0036* (2013.01); *G01N 33/24* (2013.01); *H01J 49/0463* (2013.01); *H01J 49/105* (2013.01); *H01J 49/164* (2013.01)

(58) Field of Classification Search
CPC ............... H01J 49/0036; H01J 49/0463; H01J 49/105; H01J 49/164; G01N 33/24; G01N 27/62
USPC ........................................................ 250/282
See application file for complete search history.

(56) References Cited

U.S. PATENT DOCUMENTS

2010/0313794 A1* 12/2010 Constantz ............... C04B 14/04
422/186

* cited by examiner

*Primary Examiner* — Kiet T Nguyen
(74) *Attorney, Agent, or Firm* — Millen, White, Zelano & Branigan, P.C.; William Nixon; Wan-Ching Montfort

(57) ABSTRACT

The present disclosure provides a method for simultaneously measuring the value of forsterite and trace elements in olivine, comprising the following steps: Step S1: selecting samples, wherein the samples are olivine samples; Step S2: placing the samples in a sample chamber of LA-ICP-MS, and adjusting the position of the samples in the optical axis direction so that the laser beam is well focused; Step S3: optimizing the instrument to make the signal-to-noise ratio of $^{57}$Fe be the best; Step S4: adopting LA-ICP-MS peak hopping mode and receiving all the mass peaks of the samples by single electron multiplier (SEM). The present disclosure overcomes the disadvantages of long test cycle and high test cost in the prior art.

5 Claims, 2 Drawing Sheets

METHOD FOR SIMULTANEOUSLY MEASURING THE VALUE OF FORSTERITE AND TRACE ELEMENTS IN OLIVINE

CROSS REFERENCE TO RELATED APPLICATION

This application claims the priority of Chinese Patent Application No. 202010404435.8, entitled "Method for simultaneously measuring the value of forsterite and trace elements in olivine" filed with the China National Intellectual Property Administration on May 13, 2020, which is incorporated herein by reference in its entirety.

TECHNICAL FIELD

The disclosure relates to the field of methods for measuring the value of forsterite and trace elements in olivine, in particular to a method for simultaneously measuring the value of forsterite and trace elements in olivine.

BACKGROUND ART

Olivine is one of the most important minerals in the mantle of the earth. It is widely exist in basic rocks and mantle peridotite, and can be exist in diamonds in the form of inclusions. Therefore, it is of great significance to study olivine for understanding the dynamics and melting process of the mantle. Olivine has a relatively simple chemical composition structure $(Mg, Fe)_2SiO_4$; in general, the oxides of the three major elements MgO, FeO and $SiO_2$ can account for more than 99% of the total mass of olivine. The geochemical indexes for olivine mainly include the value of forsterite (Fo) and trace elements. The formula for calculating the Fo value of olivine is $100 \times Mg/(Mg+Fe)$, which is given in molar form. The Fo value of olivine can be used to identify the original composition of mantle magma, assess the degree of magma evolution and estimate the crystallization temperature of magma and the temperature of potential magma. Although the chemical formula of olivine is simple (only three major elements), there are still trace elements that can enter its crystal lattice, such as Ni, Mn, Ca, Al, Sc, Cr, Co, Zn, V, Y, etc. The content of these trace elements in olivine can vary from a few $ng \cdot g^{-1}$ to several thousand $\mu g \cdot g^{-1}$. The trace elements indicate an important index of mantle rock geochemistry and melting process, and can be used to track the evolution process of magma and estimate the oxygen fugacity and temperature of the melt.

Accurate acquisition of the Fo value and trace element content in olivine is a prerequisite to ensure its geological application. At present, the main analytical techniques include: Electron Probe Microanalysis (EPMA), High Precision-Electron Probe Microanalysis (HP-EMPA) and Laser Ablation-Inductively Coupled Plasma-Mass Spectrometry (LA-ICP-MS). The EPMA has advantages when testing major elements (used to calculate Fo value), and has a disadvantage that due to the relatively high detection limit ($>200\ g \cdot g^{-1}$), most trace elements (such as Sc, Zn, Y, etc.) cannot be accurately analyzed. The HP-EPMA is an improved and optimized EPMA, which can simultaneously measure the Fo value and certain trace elements ($>10\ g \cdot g^{-1}$), but it has high requirements for laboratory conditions, and has a long test time and a high cost. The LA-ICP-MS has an advantage of low detection limit, which can be as low as 1.0 $g \cdot g^{-1}$ or less, but it is rarely used for the analysis of major elements (used to calculate the Fo value).

At present, there are mainly two analytical methods that can meet the requirements of simultaneous determination of the Fo value and trace elements. (1) EPMA+LA-ICP-MS: the EPMA is first used to measure the Fo value of olivine, and then the LA-ICP-MS is used to measure trace elements. Due to the use of two independent instruments, the method has a long test cycle and a high cost of testing twice at the same time, and needs to strictly match the test points of the EPMA and LA-ICP-MS. (2) HP-EPMA: it reduces the detection limit of the instrument by increasing the current density of the instrument, the voltage and the integration time. Due to the increased integration time, the test time becomes longer. This technology has high requirements for laboratory conditions and sample pretreatment, and cannot accurately analyze elements with a content of less than 10 $\mu g \cdot g^{-1}$. The disclosure proposes a new method that uses LA-ICP-MS to simultaneously measure the Fo value and trace elements.

SUMMARY

In order to solve the problems in the prior art, the present disclosure provides a method for simultaneously measuring the value of forsterite and trace elements in olivine, which solves the problems of long test cycle and high test cost in the prior art.

The technical solution adopted by the present disclosure is a method for simultaneously measuring the value of forsterite and trace elements in olivine, comprising the following steps:

Step S1: selecting samples, and the samples are olivine samples;

Step S2: placing the samples in a sample chamber of LA-ICP-MS, and adjusting the position of the samples in the optical axis direction so that the laser beam is well focused;

Step S3: optimizing the instrument to make the signal-to-noise ratio of $^{57}Fe$ be the best;

Step S4: adopting LA-ICP-MS peak hopping mode and receiving all the mass peaks of the samples by single electron multiplier (SEM);

Step S5: performing the test for 8 unknown samples, 2 standard materials and 1 quality monitoring sample in sequence and repeatedly under the condition that the standard materials and the unknown samples are measured under the same conditions;

Step S6: after obtaining the individual element signal data, calculating the Fe/Mg fractionation factor according to the Fe/Mg measured value and standard value of the standard material, and then correcting the Fe/Mg ratio of the unknown sample; and Step S7: calculating the Fo data through the conversion relationship between Fe/Mg and Fo, and calculating other trace elements through correction of the corresponding formula.

In one embodiment, the samples in step S1 are single-particle minerals and are prepared into epoxy resin sample targets with a diameter of 1 inch and a thickness of 5 mm, and the samples can also be prepared into common rock flakes with a length of 2 inch, a width of 1 inch and a thickness of 30-50 μm.

In one embodiment, the Fe/Mg ratio in step S6 is calculated by the following formula:

$$\frac{Fe}{Mg_{olivine}} = \frac{\text{signal ratio}\left(\frac{Fe}{Mg_{olivine}}\right)}{\text{signal ratio}\left(\frac{Fe}{Mg_{GOR132-G}}\right)} \times 0.5812.$$

wherein 0.5812 is a recommended value of the Fe/Mg ratio of the GOR132-G glass standard material.

In one embodiment, the formula for calculating the Fo value in step S7 is:

$$Fo = \frac{100}{1 + \frac{Fe}{Mg} \times 0.4352}.$$

wherein 0.4352 is a conversion factor of the Fe/Mg ratio between molar form and mass form.

In one embodiment, the formula for calculating the other trace elements in step S7 is:

$$C_{el|olivine} = \frac{\text{signal intensity}(el)}{\text{signal intensity}(Mg)}\bigg|_{olivine} \times \frac{\text{signal intensity}(Mg)}{\text{signal intensity}(el)}\bigg|_{GOR132-G} \times \frac{C_{el}}{C_{Mg}}\bigg|_{GOR132-G} \times C_{Mg|olivine}$$

wherein C represents the content of a certain element, and el represents the element to be measured.

In the present disclosure, using the method for simultaneously measuring the value of forsterite and trace elements in olivine has the following beneficial effects:

1. The object of the present disclosure is to obtain accurate Fo value and trace elements data using LA-ICP-MS by a series of technical measures, to provide more favorable technical support for the application of olivine geochemistry.

2. The core of the present disclosure is to integrate the current trace element measurement mode by LA-ICP-MS and apply a unique algorithm, so that the Fo value and trace elements can be accurately obtained by LA-ICP-MS at the same time, which overcomes the disadvantages of long test cycle and high test cost in the prior art.

DETAILED DESCRIPTION OF THE EMBODIMENTS

The following describes the specific embodiments of the present disclosure to help those skilled in the art to understand the present disclosure, but it should be clear that the present disclosure is not limited to the scope of the specific embodiments, for those skilled in the art, as long as various changes are within the spirit and scope of the present disclosure defined and measured by the appended claims, those changes are obvious. All inventions and creations using the concept of the present disclosure are claimed.

Figure 1:
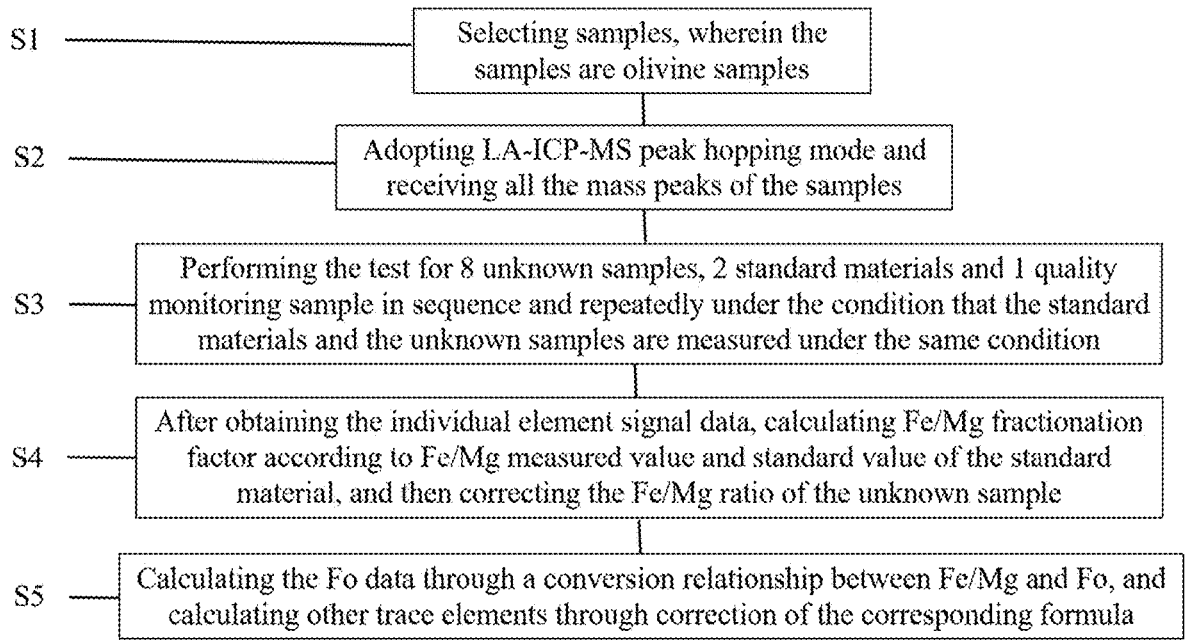
FIG. 1 shows a test flow chart of the method for simultaneously measuring forsterite value and trace elements in olivine according to the present disclosure.
Figure 2:
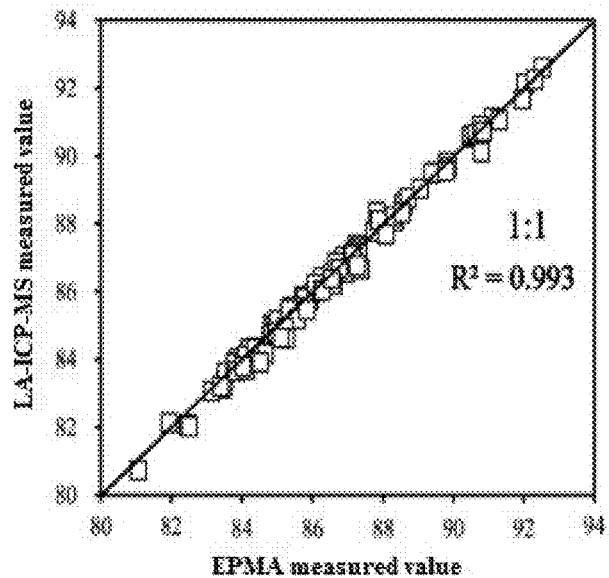
FIG. 2 is a comparison diagram of the Fo value data of LA-ICP-MS and EPMA in 150 actual olivine samples obtained by using the method for simultaneously measuring the value of forsterite and trace elements in olivine according to the present disclosure.
Figure 3:
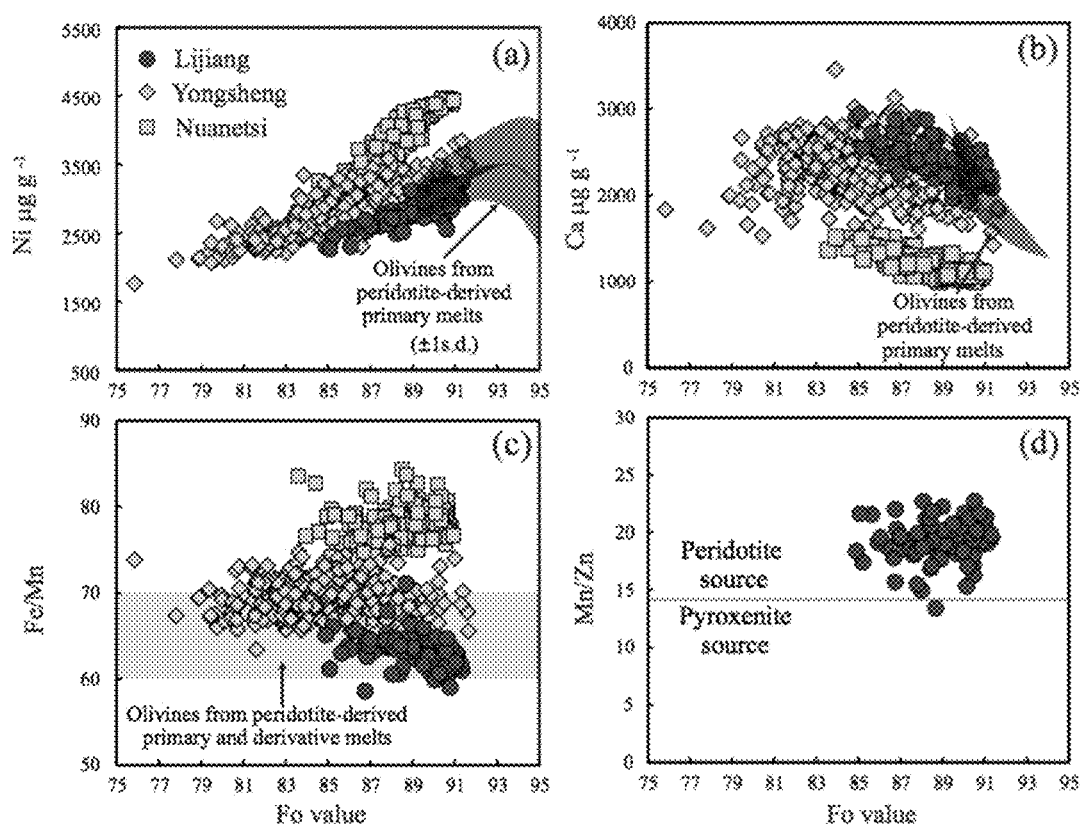
FIGS. 3(a)-3(d) are diagrams showing the application of the method for simultaneously measuring the value of forsterite and trace elements in the olivine of the present disclosure to the Lijiang olivine in Emei Mountain.

As shown in FIGS. 1-3, taking two olivine standard materials (MongOLSh11-2 and XEN) and a set of olivine in the picrite of Mount Emei as examples (as shown in step S1 of FIG. 1), the specific implementation of the technical method of the present disclosure is introduced. The Fo value and trace elements of two olivine standard materials have been reported in the art. The Fo values of a set of olivine (N=150) in the picrite of Mount Emei have been characterized by EPMA, showing that the Fo values vary from 81 to 93. These known Fo values and trace elements data are used as the verification standard of this method.

The above-mentioned olivine standard material is poured into a sample target with epoxy resin, and slightly polished to expose a cutting surface of the olivine, and then polished additionally, washed and dried to obtain an olivine standard material sample target for use.

Some rock samples are made into ordinary thin flakes to obtain an actual olivine sample target for use.

The olivine standard material sample target and the actual olivine sample target are placed into the LA-ICP-MS instrument, and purged with helium to make the samples filled with helium. As shown in step S2 of FIG. 1, the method adopts a LA-ICP-MS peak hopping mode and receives all the mass peaks of the samples.

A laser beam spot is adjusted to be circular with a diameter of 44 μm, with a laser energy density of 4 J·cm$^{-2}$, and an ablation frequency of 5 Hz.

The instrument is optimized by GOR132-G glass standard material to make the signal-to-noise ratio of $^{57}$Fe be the best, with the oxide yield (ThO/Th) of less than 0.5%, the secondary ion yield (Ca$^{2+}$/Ca$^{+}$) of less than 1.0%, and Th$^{+}$/U$^{+}$ of 0.95-1.05.

In the present disclosure, the ions to be measured and the mass numbers to be characterized are $^{7}$Li, $^{23}$Na, $^{25}$Mg, $^{27}$Al, $^{29}$Si, $^{31}$P, $^{43}$Ca, $^{45}$Sc, $^{49}$Ti, $^{51}$V, $^{53}$Cr, $^{55}$Mn, $^{57}$Fe, $^{59}$Co, $^{60}$Ni, $^{63}$Cu, $^{66}$Zn, $^{69}$Ga and $^{89}$Y respectively, with a measurement integration time of 10 milliseconds.

As shown in S3 of FIG. 1, the signal is collected in the single-point ablation mode. The collection procedure includes the instrument blank of 15 seconds, the laser ablation data of 40 seconds, and the instrument blank of 15 seconds in sequence. After every 8 unknown samples are tested, 2 GOR132-G glass standard materials, 1 MongOLSh11-2 and 1 XEN are tested in sequence, to ensure that the standard materials and unknown samples are measured under the same conditions.

In steps S4-S5 of FIG. 1, after obtaining the individual element signal data, a Fe/Mg fractionation factor is calculated according to Fe/Mg measured value and standard value of the standard material, and then correcting a Fe/Mg ratio of the unknown sample, and a Fo data is calculated through the conversion relationship between Fe/Mg and Fo, and other trace elements are calculated through correction of the corresponding formula.

The data processing process is as follows: the data is processed offlinely by Iolite software (version 3.7) and Excel (2016), wherein the Iolite is used for signal blank subtraction, instrument signal drift correction, element ratio calculation, etc; the Excel is used for the conversion of the Fe/Mg ratio and the Fo value. The inclusion in minerals should be avoided as far as possible when the signal integration interval is selected. The ratio of Fe/Mg in the sample is calculated by the following formula, $$\frac{Fe}{Mg_{olivine}} = \frac{\text{signal ratio}\left(\frac{Fe}{Mg_{olivine}}\right)}{\text{signal ratio}\left(\frac{Fe}{Mg_{GOR132-G}}\right)} \times 0.5812. \quad (1)$$

wherein the Fe/Mg ratio is given in mass form, and 0.5812 is a recommended value of the Fe/Mg ratio of the GOR132-G glass standard material.

The formula for calculating the Fo value given in molar form can be written as the following formula in mass form, $$Fo = \frac{100}{1 + \frac{Fe}{Mg} \times 0.4352}. \quad (2)$$

wherein the constant 0.4352 is a conversion factor of the Fe/Mg ratio between molar form and mass form. It can be seen from this formula that the Fo value can be obtained as long as the Fe/Mg ratio is known.

For olivine samples, the total mass of the three major elements (given in the form of oxides, i.e. MgO, SiO$_2$ and FeO) can usually account for more than 99% of the total mass of olivine. Thus, we assume herein that the total mass of MgO, SiO$_2$ and FeO is 100%, as shown in the following formula, $$MgO + FeO + SiO_2 = 100 \text{ wt. \%} \quad (3)$$

Based on the chemical formula of olivine [(Mg,Fe)$_2$SiO$_4$], the following formula can be obtained, $$\frac{MgO}{80.608} + \frac{FeO}{143.688} = \frac{SiO_2}{60.084}. \quad (4)$$

The formula for calculating Fo in mole form can be rewritten as element oxide form (MgO, SiO$_2$ and FeO), showing as follows, $$\frac{FeO}{MgO} = \left(\frac{100}{Fo} - 1\right) \times 1.7826 \quad (5)$$

Formula (6) can be obtained by formulas (3), (4) and (5), $$MgO = \frac{100 \times Fo}{252.79 - 0.7826 \times Fo} \quad (6)$$

It can be seen from this formula that when the Fo value is known, the MgO content can be calculated. In the present disclosure, Fo is calculated by formula (1) and formula (2), which is obtained by calculating the ratio of Fe/Mg. The accuracy of the MgO content calculated by formula (6) is within 1.5%.

Other trace elements are calculated by formula (7), $$C_{el|olivine} = \frac{\text{signal intensity}(el)}{\text{signal intensity}(Mg)}\bigg|_{olivine} \times \frac{\text{signal intensity}(Mg)}{\text{signal intensity}(el)}\bigg|_{GOR132-G} \times \frac{C_{el}}{C_{Mg}}\bigg|_{GOR132-G} \times c_{Mg|olivine} \quad (7)$$

wherein C represents the content of a certain element, and el represents the content of an element to be measured. The element content of Mg is calculated by MgO content obtained by formula (6) with an oxide conversion coefficient of 1.6583. Through the data processing method of the present disclosure, the Fo value and the trace elements data can be obtained at the same time.

1) MongOLSh11-2 and XEN are used as quality monitoring materials, and the measured results of their Fo and trace elements are shown in Tables 1-2.

TABLE 1

Fo value data of MongOLSh11-2 and XEN

|  | MongOLSh11-2 | 2 s | XEN | 2 s |
|---|---|---|---|---|
| recommended value | 89.53 | 0.05 | 90.78 | 0.06 |
| actual value1 | 89.61 | 0.09 | — | — |
| actual value2 | 89.50 | 0.13 | 90.70 | 0.12 |
| actual value3 | 89.61 | 0.09 | 90.80 | 0.08 |
| actual value4 | 89.52 | 0.16 | 90.64 | 0.11 |
| actual value5 | 89.51 | 0.14 | 90.67 | 0.12 |
| actual value6 | 89.51 | 0.08 | 90.82 | 0.08 |

TABLE 2

Trace element data of MongOLSh11-2 and XEN

|  | recommended value | | MongOL Sh11-2 measured value (N = 120) | | recommended value | | XEN measured value (N = 98) | |
|---|---|---|---|---|---|---|---|---|
|  | content (µg g$^{-1}$) | 2 s. (µg g$^{-1}$) | average value (µg g$^{-1}$) | 2 s (µg g$^{-1}$) | content (µg g$^{-1}$) | 2 s (µg g$^{-1}$) | average value (µg g$^{-1}$) | 2 s (µg g$^{-1}$) |
| Li | 2.18 | 0.40 | 1.56 | 0.30 | — | — | 1.21 | 0.34 |
| Na | 130 | 24 | 101 | 26 | 15$^b$ | 15$^b$ | — | — |
| Al | 245 | 34 | 266 | 14 | 46.0$^a$/43.0$^b$ | 6.0$^a$/8.0$^b$ | — | — |
| P | 66.4 | 20 | 66.4 | 11 | 37.0$^a$/17.0$^b$ | 2.0$^a$/5.0$^b$ | 42.6 | 12.2 |
| Ca | 688 | 59 | 706 | 32 | 246$^a$/239$^b$ | 19$^a$/7$^b$ | 266 | 57 |
| Sc | 3.40 | 0.20 | 3.39 | 0.10 | — | — | 2.03 | 0.13 |
| Ti | 40.2 | 6.0 | 41.7 | 1.3 | 11.0$^a$/10.0$^b$ | 1.0$^a$/4.0$^b$ | 10.8 | 1.1 |
| V | 5.5 | 0.5 | 5.2 | 0.1 | — | — | 1.87 | 0.16 |
| Cr | 125 | 9 | 123 | 5 | 40.0$^b$ | 5.0$^b$ | 40.0 | 1.7 |
| Mn | 1119 | 47 | 1133 | 33 | 1043$^a$/1032$^b$ | 15$^a$/6$^b$ | 1050 | 34 |
| Co | 148 | 12 | 139 | 3 | 145$^a$/149$^b$ | 2$^a$/8$^b$ | 135 | 6 |
| Ni | 2822 | 87 | 2717 | 57 | 3166$^a$/3132$^b$ | 55$^a$/31$^b$ | 2995 | 63 |
| Cu | 1.13 | 0.18 | 1.09 | 0.06 | — | — | 0.59 | 0.06 |
| Zn | 56.3 | 4.6 | 56.3 | 6.1 | 44.0$^a$/43.0$^b$ | 2.0$^a$/6.0$^b$ | 37.4 | 11.4 |

TABLE 2-continued

Trace element data of MongOLSh11-2 and XEN

| | recommended value | MongOL Sh11-2 measured value (N = 120) | | | recommended value | XEN measured value (N = 98) | | |
|---|---|---|---|---|---|---|---|---|
| | content ($\mu g\ g^{-1}$) | 2 s. ($\mu g\ g^{-1}$) | average value ($\mu g\ g^{-1}$) | 2 s ($\mu g\ g^{-1}$) | content ($\mu g\ g^{-1}$) | 2 s ($\mu g\ g^{-1}$) | average value ($\mu g\ g^{-1}$) | 2 s ($\mu g\ g^{-1}$) |
| Ga | 0.10 | 0.02 | 0.12 | 0.02 | — | — | 0.060 | 0.060 |
| Y | 0.079 | 0.014 | 0.074 | 0.005 | — | — | 0.030 | 0.030 |

It can be seen from the above data tables that the Fo values obtained by this method, i.e. the data in Tables 1-2, are consistent with the respective reference values within the error range.

In order to further verify that the present disclosure is also applicable to the measurement of Fo value in a wider range, we analyzed 150 actual olivine samples, which have been characterized by the Fo value by electron probe, and the results are shown in FIG. 2.

The data shows that the Fo value measured by the present disclosure is in good agreement with the EPMA data. The above results indicate that the Fo value and trace element data of olivine can be measured simultaneously by using the method of the present disclosure. It can provide an important technical support for olivine geochemical research.

This method can effectively overcome the shortcomings of the prior art: 1. Long test cycle; 2. High cost.

The technology of the present disclosure is applied to Lijiang olivine in Mount Emei, and the result is shown in FIG. 3.

The data shows that Lijiang olivine is from the mantle, not from the source area of pyroxene.

The data in the above examples are all completed on the LA-ICP-MS of GeoLas HD 193 excimer laser in series with Elemnet XR ICP-MS. The examples are only used to illustrate the present disclosure, not to limit the present disclosure. Those skilled in the art can obtain the same results on similar LA-ICP-MS according to this method.

What is claimed is:

1. A method for simultaneously measuring the value of forsterite and trace elements in olivine, comprising the following steps:
    Step S1: selecting samples, wherein the samples are olivine samples;
    Step S2: adopting LA-ICP-MS peak hopping mode and receiving all the mass peaks of the samples;
    Step S3: performing the test for 8 unknown samples, 2 standard materials and 1 quality monitoring sample in sequence and repeatedly under the condition that the standard materials and the unknown samples are measured under the same condition;
    Step S4: after obtaining the individual element signal data, calculating Fe/Mg fractionation factor according to Fe/Mg measured value and standard value of the standard material, and then correcting a Fe/Mg ratio of the unknown sample; and
    Step S5: calculating a Fo data through the conversion relationship between Fe/Mg and Fo, and calculating other trace elements through correction of the corresponding formula.

2. The method for simultaneously measuring the value of forsterite and trace elements in olivine according to claim 1, wherein the samples in step S1 are single-particle minerals and are prepared into epoxy resin sample targets with a diameter of 1 inch and a thickness of 5 mm, and the samples can also be prepared into common rock flakes with a length of 2 inch, a width of 1 inch and a thickness of 30-50 μm.

3. The method for simultaneously measuring the value of forsterite and trace elements in olivine according to claim 1, wherein the Fe/Mg ratio in step S4 is calculated by the following formula:

$$\frac{Fe}{Mg_{olivine}} = \frac{\text{signal ratio}\left(\frac{Fe}{Mg_{olivine}}\right)}{\text{signal ratio}\left(\frac{Fe}{Mg_{GOR132-G}}\right)} \times 0.5812,$$

wherein 0.5812 is a recommended value of the Fe/Mg ratio of GOR132-G glass standard material.

4. The method for simultaneously measuring the value of forsterite and trace elements in olivine according to claim 1, wherein the formula for calculating the Fo value in step S5 is:

$$Fo = \frac{100}{1 + \frac{Fe}{Mg} \times 0.4352},$$

wherein 0.4352 is a conversion factor of the Fe/Mg ratio between molar form and mass form.

5. The method for simultaneously measuring the value of forsterite and trace elements in olivine according to claim 1, wherein the formula for calculating the other trace elements in step S5 is:

$$C_{el|olivine} = \frac{\text{signal intensity}(el)}{\text{signal intensity}(Mg)}\bigg|_{olivine} \times \frac{\text{signal intensity}(Mg)}{\text{signal intensity}(el)}\bigg|_{GOR132-G} \times \frac{C_{el}}{C_{Mg}}\bigg|_{GOR132-G} \times C_{Mg|olivine},$$

wherein C represents the content of a certain element, and el represents an element to be measured.

* * * * *